(12) United States Patent
Kinser

(10) Patent No.: US 10,775,335 B2
(45) Date of Patent: Sep. 15, 2020

(54) NANOPATTERNED BIOSENSOR ELECTRODE FOR ENHANCED SENSOR SIGNAL AND SENSITIVITY

(71) Applicant: International Business Machines Corporation, Armonk, NY (US)

(72) Inventor: Emily R. Kinser, Poughkeepsie, NY (US)

(73) Assignee: International Business Machines Corporation, Armonk, NY (US)

(*) Notice: Subject to any disclaimer, the term of this patent is extended or adjusted under 35 U.S.C. 154(b) by 112 days.

(21) Appl. No.: 16/169,635

(22) Filed: Oct. 24, 2018

(65) Prior Publication Data

US 2019/0056343 A1 Feb. 21, 2019

Related U.S. Application Data

(62) Division of application No. 15/419,524, filed on Jan. 30, 2017, now Pat. No. 10,161,898.

(51) Int. Cl.
*G01N 27/327* (2006.01)
*C25D 1/00* (2006.01)
(Continued)

(52) U.S. Cl.
CPC ......... *G01N 27/3271* (2013.01); *C12Q 1/006* (2013.01); *C25D 1/006* (2013.01); *C25D 1/20* (2013.01); *C25D 5/022* (2013.01); *C25D 5/48* (2013.01); *C25D 7/123* (2013.01); *G01N 27/3276* (2013.01)

(58) Field of Classification Search
None
See application file for complete search history.

(56) References Cited

U.S. PATENT DOCUMENTS

| 2,933,458 A | 4/1960 | King et al. |
| 5,136,630 A | 8/1992 | Breneman et al. |

(Continued)

FOREIGN PATENT DOCUMENTS

| CN | 1598694 A | 3/2005 |
| CN | 106094426 A | 11/2016 |
| KR | 1020160092635 A | 8/2016 |

OTHER PUBLICATIONS

Padmanabhan, J., et al., "Engineering Cellular Response Using Nanopatterned Bulk Metallic Glass", American Chemical Society Nano, Apr. 2014, pp. 4366-4375, vol. 8, No. 5.

(Continued)

*Primary Examiner* — Louis J Rufo
(74) *Attorney, Agent, or Firm* — Scully, Scott, Murphy & Presser, P.C.; Steven J. Meyers

(57) ABSTRACT

Methods for forming an electrode structure, which can be used as a biosensor, are provided in which the electrode structure has non-random topography located on one surface of an electrode base. In some embodiments, an electrode structure is obtained that contains no interface between the non-random topography of the electrode structure and the electrode base of the electrode structure. In other embodiments, electrode structures are obtained that have an interface between the non-random topography of the electrode structure and the electrode base of the electrode structure.

20 Claims, 12 Drawing Sheets

(51) Int. Cl.
  *C25D 1/20* (2006.01)
  *C12Q 1/00* (2006.01)
  *C25D 5/02* (2006.01)
  *C25D 5/48* (2006.01)
  *C25D 7/12* (2006.01)

(56) References Cited

U.S. PATENT DOCUMENTS

| | | |
|---|---|---|
| 6,359,444 B1 | 3/2002 | Grimes |
| D469,540 S | 1/2003 | Holker et al. |
| 6,914,279 B2 | 7/2005 | Lu et al. |
| 7,005,048 B1 | 2/2006 | Watanabe et al. |
| 7,294,910 B2 | 11/2007 | Thomas et al. |
| 7,524,408 B2 | 4/2009 | Monbouquette et al. |
| 7,604,592 B2 | 10/2009 | Freeman et al. |
| 7,627,938 B2 * | 12/2009 | Kim ............... A61K 9/0021 29/17.3 |
| 7,894,914 B2 | 2/2011 | Stahmann et al. |
| 7,949,382 B2 | 5/2011 | Jina |
| 7,955,483 B2 | 6/2011 | Gu et al. |
| 8,076,125 B2 | 12/2011 | McGimpsey |
| 8,097,926 B2 | 1/2012 | De Graff et al. |
| 8,221,822 B2 | 7/2012 | Flanagan et al. |
| 8,303,800 B2 | 11/2012 | Fukuda et al. |
| 8,485,245 B1 | 7/2013 | Prest et al. |
| 8,529,835 B2 | 9/2013 | Kaplan et al. |
| 8,668,978 B2 | 3/2014 | Malima et al. |
| 8,741,380 B2 | 6/2014 | Yoshida et al. |
| 8,772,228 B2 | 7/2014 | Stupp et al. |
| 8,808,516 B2 | 8/2014 | Melosh et al. |
| 8,907,384 B2 * | 12/2014 | Pace ............... B82Y 15/00 257/253 |
| 9,958,441 B2 | 5/2018 | Zhang et al. |
| 2005/0269285 A1 | 12/2005 | Jung et al. |
| 2007/0148653 A1 * | 6/2007 | Yoshida ............ B29C 33/3842 435/6.11 |
| 2009/0137423 A1 | 5/2009 | Higson |
| 2009/0155800 A1 | 6/2009 | Hong et al. |
| 2009/0243584 A1 | 10/2009 | Zhang et al. |
| 2009/0272285 A1 | 11/2009 | Kraus et al. |
| 2010/0006451 A1 | 1/2010 | Gordon et al. |
| 2010/0066346 A1 * | 3/2010 | Zhang ............... C23C 28/322 324/71.1 |
| 2010/0310773 A1 | 12/2010 | Yoshida et al. |
| 2010/0318193 A1 | 12/2010 | Desai et al. |
| 2011/0027458 A1 | 2/2011 | Boock et al. |
| 2011/0073475 A1 | 3/2011 | Kastanos et al. |
| 2011/0091510 A1 | 4/2011 | Lele et al. |
| 2011/0230735 A1 | 9/2011 | Wolfe et al. |
| 2011/0233063 A1 * | 9/2011 | Seki ............... C25D 1/10 205/70 |
| 2011/0301716 A1 | 12/2011 | Sirivisoot et al. |
| 2011/0319734 A1 | 12/2011 | Gottlieb et al. |
| 2012/0218550 A1 | 8/2012 | O'Mahony |
| 2012/0312061 A1 | 12/2012 | Pham et al. |
| 2013/0025814 A1 | 1/2013 | Demetriou et al. |
| 2013/0079608 A1 | 3/2013 | Miller et al. |
| 2013/0112321 A1 | 5/2013 | Poole et al. |
| 2013/0150822 A1 | 6/2013 | Ross |
| 2014/0230854 A1 | 8/2014 | Lopez et al. |
| 2014/0238574 A1 | 8/2014 | Kinser |
| 2016/0331290 A1 * | 11/2016 | Oh ............... A61B 5/0538 |
| 2017/0025453 A1 | 1/2017 | Bornfreund et al. |
| 2017/0202079 A1 | 7/2017 | Norton et al. |
| 2017/0209079 A1 | 7/2017 | Kinser et al. |
| 2017/0241003 A1 | 8/2017 | Na et al. |
| 2018/0020957 A1 | 1/2018 | Kinser |
| 2018/0217080 A1 | 8/2018 | Kinser |
| 2018/0252662 A1 | 9/2018 | Kinser |
| 2019/0056343 A1 | 2/2019 | Kinser |
| 2019/0142310 A1 | 5/2019 | Kinser et al. |
| 2020/0077956 A1 | 3/2020 | Kinser |

OTHER PUBLICATIONS

Zhai, D. et al., "Highly Sensitive Glucose Sensor Based on Pt Nanoparticle/Polyaniline Hydrogel Heterostructures", ACS Nano, Mar. 2013, pp. 3540-3546, vol. 7, No. 4.

S.-H. Parng, et al. "Effect of temperature and glucose concentration on a glass-based sensor for long-term stability investigation", J. Micro/Nanolith. MEMS MOEMS, Jan.-Mar. 2011, pp. 013003-1 to 013003-5, vol. 10(1).

J. Gajdzik, et al., "Enzyme immobilisation on self-organised nanopatterned electrode surfaces", Phys. Chem. Chem. Phys., Sep. 2010, pp. 12604-12607, 12.

M. Cardosi, et al., "Amperometric Glucose Sensors for Whole Blood Measurement Based on Dehydrogenase Enzymes", Intech, Dehydrogenases, Chapter 13, Published: Nov. 14, 2012, pp. 319-354.

D. C. Deshpande, et al., "Development of a nanoscale heterostructured glucose sensor using modified microfabrication processes", J. Micro/Nanolith, Apr.-Jun. 2008, MEMS MOEMS, pp. 023005-1 to 023005-6, vol. 7(2).

Freckmann, G., et al.,"System Accuracy Evaluation of 27 Blood Glucose Monitoring Systems According to DIN EN ISO 15197", Diabetes Technology & Therapeutics. Mar. 2010, pp. 221-231, vol. 12, No. 3.

Browne, D. J., et al., "Comparison of nucleation and growth mechanisms in alloy solidification to those in metallic glass crystallisation—relevance to modeling", Transactions of The Indian Institute of Metals, Aug.-Oct. 2009, pp. 409-412, vol. 62, Issues 4-5.

Pitt, E. B., et al., "Temperature dependence of the thermoplastic formability in bulk metallic glasses", Journal of Applied Physics, published online Aug. 23, 2011, 110, pp. 043518-1 to 043518-7.

Mailoa, J. P., et al., "Textured Conducting Glass by Nanosphere Lithography for Increased Light Absorption in Thin-Film Solar Cells", J. Phys. D. Appl. Phys., Feb. 2014, 6 pages, vol. 47, No. 8, 058105.

Lee, S. H., et al., "Nanostructured indium-tin-oxide films fabricated by all-solution processing for functional transparent electrodes", Optics Express, Oct. 2011, pp. 21803-21808, col. 19, No. 22.

Kaushik, N., et al., "Metallic glass thin films for potential biomedical applications," Journal of Biomedical Materials Research B: Applied Biomaterials, Oct. 2014, pp. 1544-1552, vol. 102B, Issue 7.

International Search Report dated May 14, 2018 received in a corresponding foreign application.

Carmo, M., et al., "Bulk Metallic Glass Nanowire Architecture for Electrochemical Applications", American Chemical Society, Published online Mar. 3, 2011, pp. 2979-2983, vol. 5, No. 4.

"Gold! The crystal structure of success", Crystallography365, posted on Jan. 17, 2014, 4 pages.

List of IBM Patents or Patent Applications Treated as Related, dated Oct. 24, 2018, 2 pages.

Office Action dated Jun. 9, 2020 received in U.S. Appl. No. 16/245,942.

Office Action dated Jul 23, 2020 received in U.S. Appl. No. 16/169,654, copy not enclosed.

* cited by examiner

NANOPATTERNED BIOSENSOR ELECTRODE FOR ENHANCED SENSOR SIGNAL AND SENSITIVITY

BACKGROUND

The present application relates to methods of forming an electrode structure. More particularly, the present application relates to methods of forming a nanopatterned electrode structure that can be used for biosensing applications.

Biosensors with enhanced signal and sensitivity are essential to provide reliable data for both medical and environmental monitoring. Such biosensors are especially needed for areas related to food and water supply security as well as the healthcare industry. For healthcare, glucose sensors comprise a significant portion of the existing biosensor market. Platinum (Pt) is commonly used as a working electrode in glucose sensors, and platinum has demonstrated biocompatibility. External electrochemical sensors (so-called "Test-Strips") are commonly used. However, limitations exist on the accuracy and applicability of test strip sensors.

In vivo glucose sensors, which are implanted into a human body, can be used to continuously monitor blood sugar. However, the foreign body response restricts in vivo biosensors. Moreover, the foreign body response can reduce the sensor signal output over time.

Despite advances made in biosensor technology, there is still a need to provide low-cost biosensors that exhibit enhanced sensor signal and sensitivity, and which may also mitigate the foreign body response.

SUMMARY

Methods for forming an electrode structure, which can be used as a biosensor, are provided in which the electrode structure has non-random topography located on one surface of an electrode base. In some embodiments, improved sensor signal and sensitivity can be obtained in such an electrode structure if there is no interface between the non-random topography of the electrode structure and the electrode base of the electrode structure. By "no interface" is it meant that the non-random topography and the electrode base are of unitary construction (i.e., one piece) and unitary composition (i.e., a same material). Other embodiments include electrode structures that may have an interface between the non-random topography of the electrode structure and the electrode base of the electrode structure.

In one embodiment of the present application, a method of forming an electrode structure is provided that includes providing a mold having a pattern that comprises both an electrode base shape and a nanotopography shape. A metallic seed layer and a conductive metal-containing material are then formed to provide an electrode structure comprising the conductive metal-containing material and having the electrode base shape and the nanotopography shape resulting from the influence of the mold. The mold is then removed from the electrode structure, and a biological functionalization material is then added to the electrode structure.

In another embodiment of the present application, a method of forming an electrode structure is provided that includes providing an electrode base having an electrode base shape on a substrate. Next, a patterned material layer is formed surrounding the electrode base, wherein the patterned material layer contains openings for defining a nanotopography shape of the electrode structure. A metallic seed layer is then formed on exposed surfaces of the electrode base and within the openings of the patterned material layer, and thereafter a conductive metal-containing material is electroplated on the metallic seed layer and within the openings of the patterned material layer to provide the electrode structure comprising the electrode base having the electrode base shape and the conductive metal-containing material having the nanotopography shape. Next, the patterned material layer is removed, and thereafter, a biological functionalization material is attached to the electrode structure.

In yet another embodiment of the present application, a method of forming an electrode structure is provided that includes providing an electrode base material on a substrate. Next, a patterned material layer is formed surrounding the electrode base material, wherein the patterned material layer contains openings. The electrode base material exposed surface is then etched utilizing the patterned material layer as an etch-resistant mask to provide the electrode structure comprising a remaining portion of the electrode base material and having an electrode base shape and a nanotopography shape, with no interface present between the remaining portion of the electrode base material and the nanotopography. The patterned material layer is then removed, and thereafter a biological functionalization material is attached to the electrode structure.

DETAILED DESCRIPTION

Figure 1:
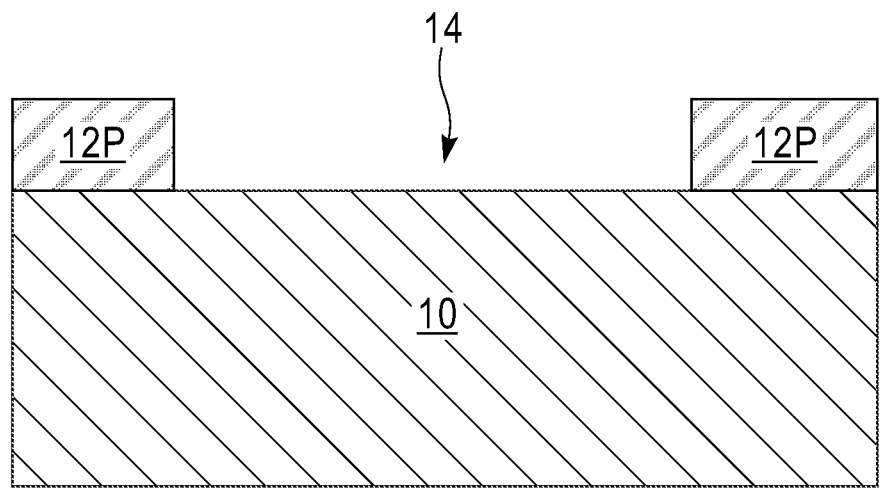
FIG. 1 is a cross sectional view of an exemplary structure including a first mask layer patterned to have an opening for defining an electrode base shape and located on a surface of a substrate in accordance with an embodiment of the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

As mentioned above, methods for forming an electrode structure, which can be used as a biosensor, are provided in which the electrode structure has non-random topography located on one surface of an electrode base. In some embodiments, improved sensor signal and sensitivity can be obtained in such an electrode structure if there is no interface between the non-random topography of the electrode structure and the electrode base of the electrode structure. By "no interface" is it meant that the non-random topography and the electrode base are of unitary construction (i.e., one piece) and unitary composition (i.e., a same material). Other embodiments include electrode structures that may have an interface between the non-random topography of the electrode structure and the electrode base of the electrode structure.

Referring first to FIGS. 1-10, there is illustrated an embodiment of the present application in which a method is disclosed for forming an electrode structure in which no interface is formed between the non-random topography of the electrode structure and the electrode base of the electrode structure.

Referring first to FIG. 1, there is illustrated an exemplary structure including a first mask layer 12P patterned to have an opening 14 for defining an electrode base shape and located on a surface of a substrate 10 in accordance with an embodiment of the present application. That is, the opening 14 has a shape that is used in the present application for defining the electrode base of a resultant electrode structure to be subsequently formed. The shape of opening 14 may also include any corresponding wiring for the electrode structure. In one embodiment, first mask layer 12P may be comprised of a photosensitive material such as a photoresist. In an alternate embodiment, first mask layer 12P may be comprised of dielectric film, hereafter referred to as a hardmask, which has been patterned using photolithography or other means known to those skilled in the art.

The substrate 10 that can be employed in the present application includes any material that can be readily patterned as described herein and that can be subsequently removed from the resultant electrode structure that is formed within a mold made from substrate 10.

In one embodiment of the present application, the substrate 10 is composed of a semiconductor material. The term "semiconductor material" denotes a material that has an electrical conductivity value between a conductor, such as copper, and an insulator, such as glass. Semiconductor materials may exist as elemental materials or compound materials. Examples of semiconductor materials that may be used as substrate 10 include Si, SiGe, SiGeC, SiC, Ge alloys, III/V compound semiconductors or II/VI compound semiconductors. In some embodiments of the present application, the substrate 10 may comprise a single semiconductor material. In other embodiments of the present application, the substrate 10 may comprise a multilayered stack of semiconductor materials.

In one embodiment of the present application, the semiconductor material that can provide substrate 10 may be a single crystalline semiconductor material such as, for example, single crystalline silicon. By "single crystalline" it is meant a material in which the crystal lattice of the entire sample is continuous and unbroken to the edges of the sample, with no grain boundaries. In another embodiment of the present application, the semiconductor material that can provide substrate 10 may be a polycrystalline semiconductor material such as, for example, polycrystalline silicon. By "polycrystalline" it is meant a material that is composed of many crystallites (i.e., grains) of varying sizes and orientation. In yet a further embodiment of the present application, the semiconductor material that can provide substrate 10 may be an amorphous semiconductor material such as, for example, amorphous silicon. By "amorphous" it is meant a material that lacks a long-range crystal order of a crystal.

In some embodiments of the present application, the semiconductor material that provides substrate 10 is a bulk semiconductor material. By "bulk" it is meant that the entirety of the substrate 10 is composed of at least one semiconductor material. In one example, the substrate 10 is entirely composed of silicon.

Another material that may be used as substrate 10 is a dielectric material. By "dielectric material" it is meant a material (i.e., insulator) that does not conduct electricity readily. In one embodiment of the present application, the dielectric material that can provide substrate 10 is composed of a semiconductor oxide such as, for example, silicon dioxide. In another embodiment of the present application, the dielectric material that can provide substrate 10 may be composed of a semiconductor nitride such as, for example, silicon nitride. Other dielectric materials such as, for example, dielectric metal oxides, including aluminum oxide, may also be used as the material which can be used as the substrate 10.

In some embodiments, substrate 10 may be composed of a combination of a semiconductor material and a dielectric material. For example, substrate 10 may be a material stack of, from bottom to top, a silicon dioxide layer and a silicon layer. An optional handle substrate can be located beneath the silicon dioxide layer. The optional handle substrate may be composed of a semiconductor material, insulator, or conductive material.

Substrate 10 may also be composed of a ceramic material, an elemental metal, an alloy of an elemental material or any other material or combination of materials that can be readily patterned as described herein and thereafter readily removed from an electrode structure that is subsequently formed into a mold made from the material that provides substrate 10.

The first mask layer 12P that can be used in the present application may include a positive-tone photoresist material, a negative-tone photoresist material, a hybrid photoresist material, or a hardmask layer comprised of a dielectric material. In one embodiment, the first mask layer 12P can be provided by first depositing a blanket layer of photoresist material on a surface of substrate 10. Following deposition of the blanket layer of photoresist material, the blanket layer of photoresist material is patterned to have an opening 14 that defines an electrode base shape. When a hardmask layer is utilized, a blanket layer of a hardmask material (such as, silicon nitride) is first deposited and thereafter a patterned photoresist containing an opening that defines the electrode base shape is formed atop the blanket layer of hardmask material. The pattern in the patterned photoresist is then transferred to the blanket hardmask material as an intermediate step, followed by subsequent transfer of the pattern to the substrate 10. The transferring of the pattern may include one or more etching steps. The patterned photoresist can be removed from atop the hardmask material anytime after the pattern has been transferred to the blanket layer of hardmask material.

The opening 14 defining the electrode base shape is not limited to any specific shape. In one embodiment of the present application, the opening 14 (and thus the electrode base shape) is a polygonal. In such an embodiment, the opening 14 (and thus the electrode base shape) may be triangular, quadrilateral or pentagonal. In other embodiments, the opening 14 (and thus the electrode base shape) may be circular or elliptical. The opening 14 may also include additional structures such as wiring or probe pads required to read out the electrical signal from the final electrode structure (not shown), thus resulting in a compound shape for opening 14.

Figure 2:
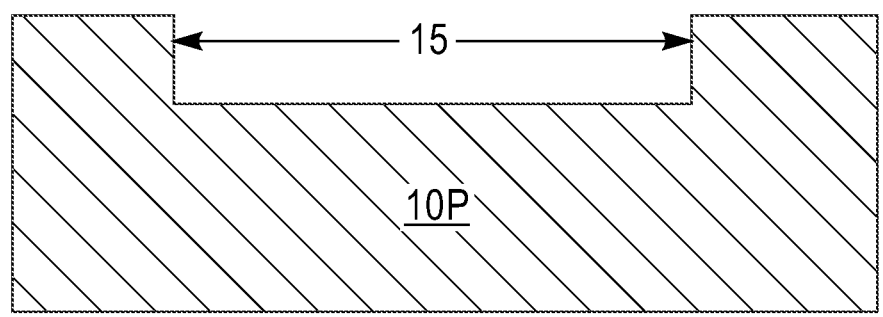
FIG. 2 is a cross sectional view of the exemplary structure of FIG. 1 after transferring the electrode base shape into the substrate to provide a patterned substrate having the electrode base shape and removing the first mask layer from the resultant structure.

Referring now to FIG. 2, there is illustrated the exemplary structure of FIG. 1 after transferring the electrode base shape into the substrate 10 to provide a patterned substrate 10P having the electrode base shape 15 and removing the first mask layer 12P from the resultant patterned substrate 10P. As is shown, the electrode base shape 15 does not extend through the entirety of the original substrate 10. Instead, some portion of the original substrate 10 remains beneath the electrode base shape 15 after the pattern transfer process.

The transferring of the electrode base shape 15 defined by opening 14 into the substrate 10 may be performed utilizing one or more etching processes. Examples of etching processes that may be used in the present application to transfer the electrode base shape 15 into the substrate 10 may include dry etching, wet etching or any combination thereof. Dry etching may include one of reactive ion etching (RIE), ion beam etching, plasma etching, or laser ablation. Wet etching may include a chemical etchant that is selective in removing the material that provides the substrate 10 relative to the mask layer material. The first mask layer 12P can be removed from the patterned substrate 10P utilizing any conventional resist stripping process such as, for example, oxygen ashing or other chemical means. In some embodiments, a planarization process may be used to remove the first mask layer 12P.

Figure 3:
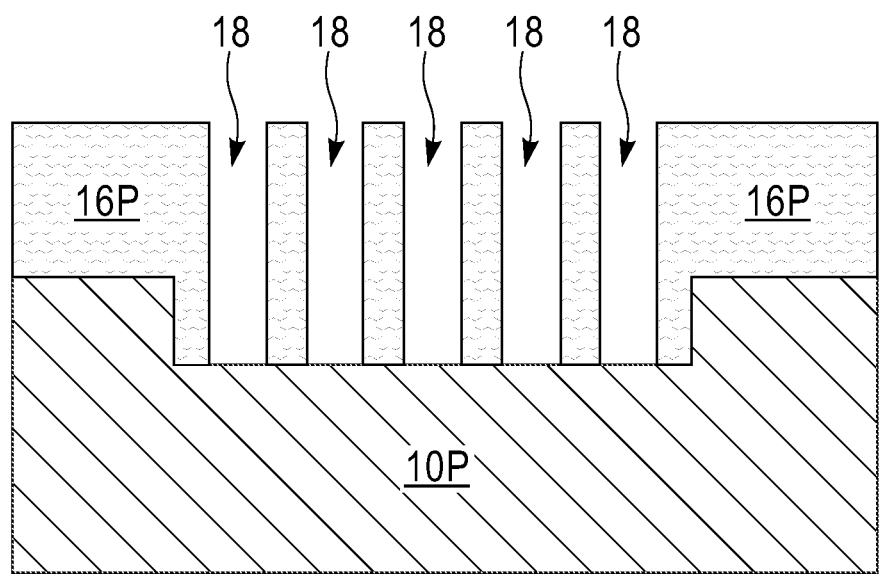
FIG. 3 is a cross sectional view of the exemplary structure of FIG. 2 after forming a second mask layer patterned to have a plurality of openings that collectively define a nanotopography shape on the patterned substrate.

Referring now to FIG. 3, there is illustrated the exemplary structure of FIG. 2 after forming a second mask layer 16P patterned to have a plurality of openings 18 that collectively define a nanotopography shape on the patterned substrate 10P. By "nanotopography shape" it is meant an array of non-random (i.e., regular repeating) individual articulated features whose size is less than the size of the electrode base shape 15. In a preferred embodiment, at least one dimension of the nanotopography shape is less 1 um in size.

The plurality of openings 18 may have various shapes and sizes. For example, the plurality of openings 18 may have a shape of a circle, an ellipse, or an annular structure. In one embodiment of the present application, the plurality of openings 18 that is provided may have a critical dimension, i.e., diameter or width, from 5 nm to 900 nm. In another embodiment of the present application, the plurality of openings 18 that is provided may have a critical dimension from 20 nm to 300 nm.

In one embodiment of the present application, each opening of the plurality of openings 18 has a pitch ratio of from 2:1 to 100:1. By "pitch" it is meant the center-to-center distance of nearest-neighbor features. The "pitch ratio" is defined based upon the critical dimension of the feature, where the spacing between the features is proportional to the critical dimension of the features. In another embodiment of the present application, each opening of the plurality of openings 18 has a pitch ratio of from 2:1 to 20:1.

In one embodiment of the present application, the second mask layer 16P is a photoresist material that can be formed and patterned as defined above. In another embodiment, the second mask layer 16P is a dielectric layer which can be patterned as defined above. In yet another embodiment of the present application, the second mask layer 16P is a component of a block copolymer such as, for example, a self-assembling block copolymer. Notably, some block copolymers can be processed to include an ordered pattern containing repeating structural units. In one embodiment, the block copolymer may contain any numbers of the polymeric block components A and B arranged in any manner. For example, the block copolymer can have either a linear or a branched structure. In one embodiment, the block copolymer is a linear diblock copolymer having the formula of A-B. Specific examples of suitable block copolymers that can be used for forming the structural units may include, but are not limited to: polystyrene-block-polymethylmethacrylate (PS-b-PMMA), polystyrene-block-polyisoprene (PS-b-PI), polystyrene-block-polybutadiene (PS-b-PBD), polystyrene-block-polyvinylpyridine (PS-b-PVP), polystyrene-block-polyethyleneoxide (PS-b-PEO), polystyrene-block-polyethylene (PS-b-PE), polystyrene-b-polyorganosilicate (PS-b-POS), polystyrene-block-polyferrocenyldimethylsilane (PS-b-PFS), polyethyleneoxide-block-polyisoprene (PEO-b-PI), polyethyleneoxide-block-polybutadiene (PEO-b-PBD), polyethyleneoxide-block-polymethylmethacrylate (PEO-b-PMMA), polyethyleneoxide-block-polyethylethylene (PEO-b-PEE), polybutadiene-block-polyvinylpyridine (PBD-b-PVP), and polyisoprene-block-polymethylmethacrylate (PI-b-PMMA).

In order to form the ordered pattern containing repeating structural units, the block copolymer is first dissolved in a suitable solvent system to form a block copolymer solution, which is then applied onto a surface to form a block copolymer layer, followed by annealing of the block copolymer layer, thereby effectuating phase separation between different polymeric block components, i.e., first and second units contained in the block copolymer. The segregated block copolymer can then be exposed, and developed to provide the second mask layer 16P having the plurality of openings 18.

Figure 4:
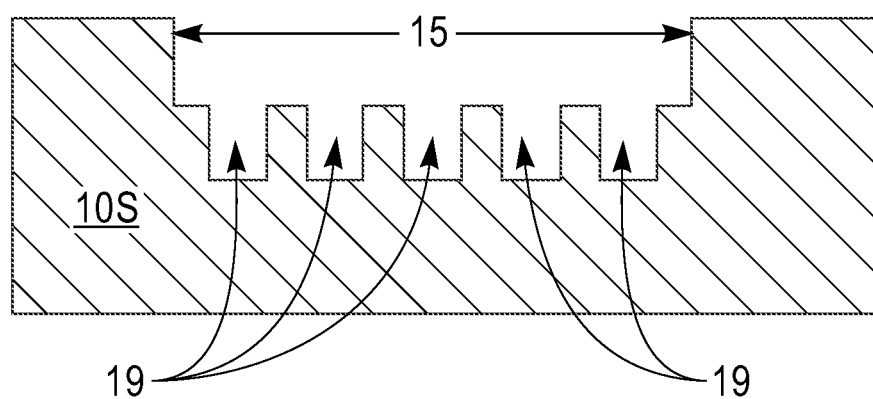
FIG. 4 is a cross sectional view of the exemplary structure of FIG. 3 after transferring the nanotopography shape into the patterned substrate to provide a mold containing the electrode base shape and the nanotopography shape and removing the second mask layer.

Referring now to FIG. 4, there is illustrated the exemplary structure of FIG. 3 after transferring the nanotopography shape provided by the plurality of openings 18 into the patterned substrate 10P to provide a mold 10S containing the electrode base shape 15 and the nanotopography shape 19 and removing the second mask layer 16P. As stated above, the nanotopography shape that is transferred into the patterned substrate 10P includes an array of non-random (i.e., regular repeating) individual articulated features (each non-random individual articulated feature is labeled as element 19 in FIG. 4) whose critical dimension is less than the size of the electrode base shape 15 provided on substrate 10.

As is shown in FIG. 4, the nanotopography shape including each non-random individual articulated feature 19 is formed within the area including the electrode base shape 15. As is also shown, the nanotopography shape including each non-random individual articulated feature 19 may not extend through the entirety of the mold 10S. Instead, some portion of the mold 10S may remain beneath each non-random individual articulated feature 19 that collectively define the nanotopography shape after the pattern transfer process. In another embodiment (not shown), the nanotopography shape may extend entirely through the thickness of mold 10S.

Each non-random individual articulated feature 19 that is formed utilizing the second mask layer 16P has a shape, width, and pitch defined by the plurality of openings 18 and the etching process used to transfer the pattern of openings 18 to the patterned substrate 10P. For example, each non-random individual articulated feature 19 may have a shape of a rod, a cone, an ellipse, or an annular structure. In one embodiment of the present application, each non-random individual articulated feature 19 may have a critical dimension ranging in size from 5 nm to 900 nm. In another embodiment of the present application, each non-random individual articulated feature 19 may have a critical dimension ranging in size from 20 nm to 300 nm.

In one embodiment of the present application, each non-random individual articulated feature 19 has a pitch ratio of from 2:1 to 100:1. In another embodiment of the present application, each non-random individual articulated feature 19 has a pitch ratio of from 2:1 to 20:1.

In one embodiment of the present application, each non-random individual articulated feature 19 has a height from 5 nm to 300 µm. In another embodiment of the present application, each non-random individual articulated feature 19 has a height from 50 nm to 20 µm.

In one embodiment of the present application, each non-random individual articulated feature 19 has an aspect ratio (i.e., ratio of width to height) of 1:1 to 500:1. In another embodiment of the present application, each non-random individual articulated feature 19 has an aspect ratio (i.e., width to height) of 2:1 to 100:1.

The height and aspect ratio of each non-random individual articulated feature 19 is determined by the depth at which each non-random individual articulated feature 19 is formed into the patterned substrate 10P.

The transferring of the nanotopography shape into the patterned substrate 10P can be achieved utilizing one of the etching processes mentioned above for transferring the electrode base shape into substrate 10. In one embodiment of the present application, and when second mask layer 16P is composed of a photoresist material, the second mask layer 16P can be removed utilizing a conventional resist developer such as, for example, ashing. In another of the present application, and when the second mask layer 16P is a component of a block copolymer or a dielectric layer, second mask layer 16P can be removed utilizing an etchant that is selective in removing the component of the block copolymer or dielectric layer.

Figure 5:
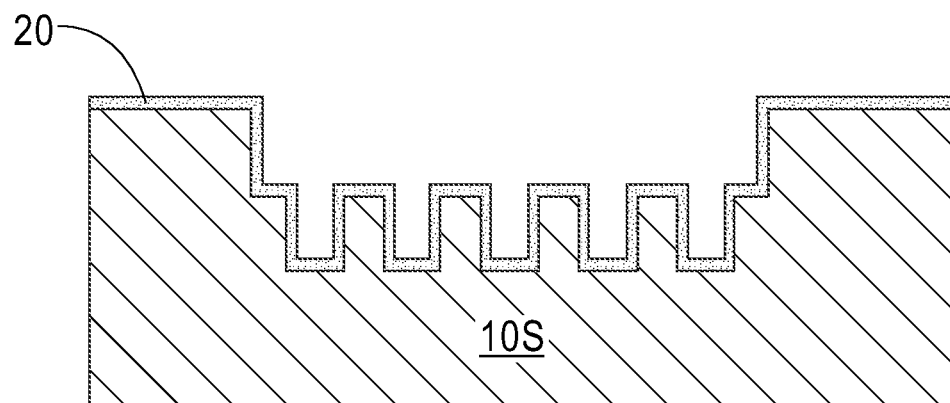
FIG. 5 is a cross sectional view of the exemplary structure of FIG. 4 after forming a metallic seed layer on the exposed surfaces of the mold.

Referring now to FIG. 5, there is illustrated the exemplary structure of FIG. 4 after forming a metallic seed layer 20 on the exposed surfaces of the mold 10S. The metallic seed layer 20 (which may also be referred to as a plating seed layer) includes any metal or metal alloy that can facilitate the subsequent electroplating of a conductive metal-containing material (to be subsequently described). The metallic seed layer 20 may include platinum, copper, silver, gold, tungsten, aluminum, iron, palladium, nickel, titanium, zirconium or any alloy thereof. The metallic seed layer 20 typically includes the same conductive metal or metal alloy as the subsequently formed conductive metal-containing material 22. For example, a copper seed layer is used for electroplating a copper layer.

The metallic seed layer 20 may have a thickness from 5 nm to 25 nm, although other thicknesses that are lesser than 5 nm, and greater than 25 nm can be used in the present application. In the illustrated embodiment of the present embodiment, the metallic seed layer 20 is continuous layer which can be formed utilizing a deposition process such as, for example, chemical vapor deposition, plasma enhanced chemical vapor deposition, atomic layer deposition or physical vapor deposition.

Figure 6:
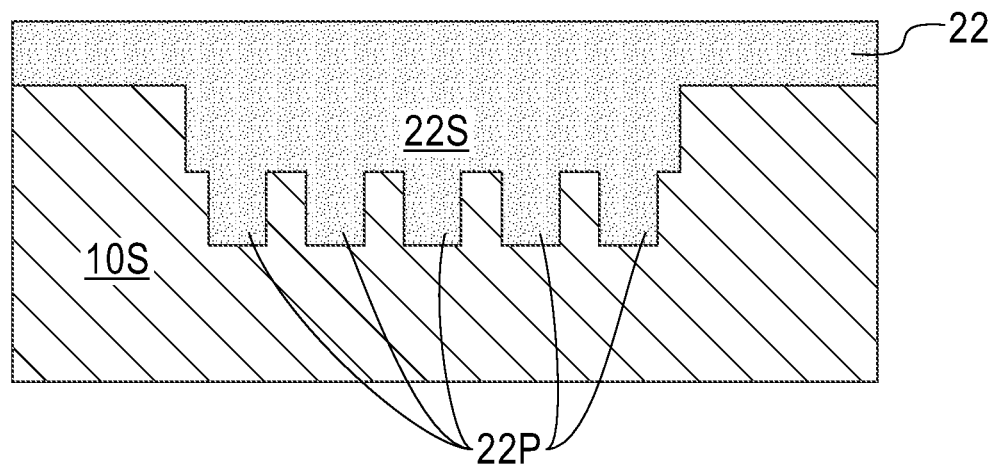
FIG. 6 is a cross sectional view of the exemplary structure of FIG. 5 after electroplating a conductive metal-containing material to provide an electrode structure comprising the conductive metal-containing material and having the electrode base shape and the nanotopography shape of the mold.

Referring now to FIG. 6, there is illustrated the exemplary structure of FIG. 5 after electroplating a conductive metal-containing material 22 on the metallic seed layer 20 to provide an electrode structure having the electrode base shape and the nanotopography shape of the mold 10S. The conductive metal-containing material 22 may consist of an elemental metal or an alloy containing one or more elemental metals. Examples of elemental metals that may be employed as the conductive metal-containing material 22 include, but are not limited to platinum, copper, silver, gold, tungsten, aluminum, iron, palladium, nickel, titanium, or zirconium. Since in an ideal embodiment the metallic seed layer 20 is composed of the same material as the conductive metal-containing material 22, the metallic seed layer 20 is not separately shown in the subsequent drawings of the present application.

As mentioned above, the conductive metal-containing material 22 is formed utilizing an electroplating process. Electroplating is a process that uses electrical current to reduce dissolved metal cations present in an electroplating bath (i.e., an electrolyte) so that the metal cations form a coherent metal coating on an electrode.

When conductive metal-containing material 22 is introduced in the electrode base shape 15, the resulting structure provides an electrode base 22S of the electrode structure, while the nanotopography shape 19 provides non-random topography in the form of repeating individually articulated features 22P of the electrode structure. In accordance with this embodiment of the present application, the electrode base 22S of the electrode structure, and the non-random topography provided by the repeating individually articulated features 22P are of unitary construction (i.e., single piece) and of a same composition. Thus, the electrode structure (22S, 22P) that is provided lacks an interface between the electrode base 22S and the non-random topography provided by the repeating individually articulated features 22P. Each repeating individually articulated feature 22P that is provided has a shape, width, pitch, height and aspect ratio as defined above for each non-random individual articulated feature 19.

Figure 7:
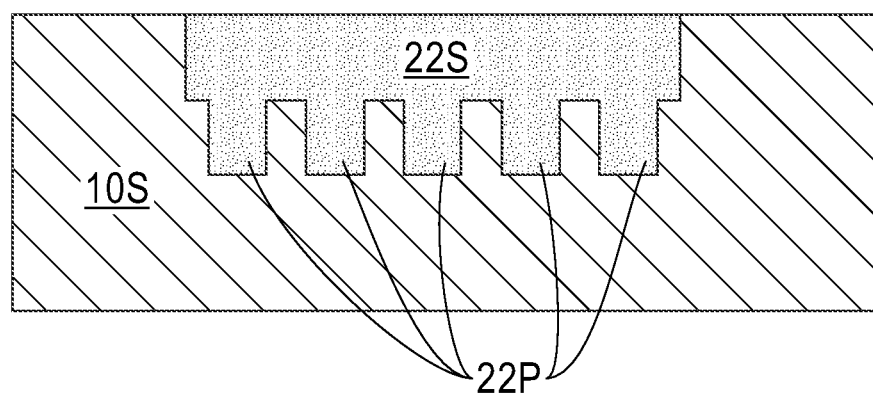
FIG. 7 is a cross sectional view of the exemplary structure of FIG. 6 after removing excess conductive metal-containing material that may be located above the electrode base shape of the mold.

Referring now to FIG. 7, there is illustrated the exemplary structure of FIG. 6 after removing excess conductive metal-containing material 22 that is located above the electrode base shape 15 of the mold 10S. After the excess conductive metal-containing material 22 is removed, the resultant electrode structure (22S, 22P) has a planar surface that is opposite the surface that includes the non-random topography in the form of repeatable non-random individually articulated features 22P.

In one embodiment of the present application, the removal of the excess conductive metal-containing material 22 may be performed by a planarization process such as, for example, chemical mechanical planarization and/or grinding. In another embodiment of the present application, the removal of the excess conductive metal-containing material 22 may be performed by utilizing at least one etch process such as, for example, a chemical etch back process and/or a reactive ion etch (RIE) process.

Figure 8:
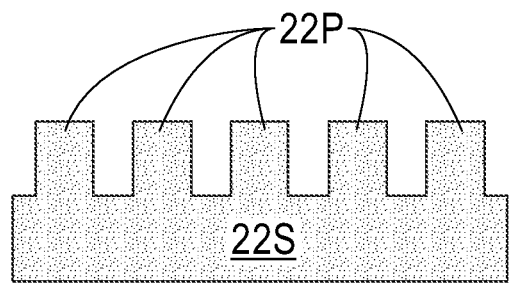
FIG. 8 is a cross sectional view of the exemplary structure of FIG. 7 after removing the mold from the electrode structure.

Referring now to FIG. 8, there is illustrated the exemplary structure of FIG. 7 after removing the mold 10S from the electrode structure (22S, 22P). In some embodiments of the present application, the mold 10S can be removed by completely dissolving the mold 10S utilizing a wet chemical etchant. In another embodiment, the mold 10S may be removed using reactive ion etching (RIE). In such embodiments, the mold 10S is a single-use mold.

In some embodiments, the mold 10S may be removed by releasing the resultant electrode structure (22S, 22P) from the mold 10S. In such an embodiment, the mold 10S may be reused multiple times. In such an instance, a release agent such as, for example, silicone, may be applied to the inside of the mold 10S prior to introducing the conductive metal-containing material 22 into the mold 10S. The release agent may include any chemical that can prevent bonding of the conductive metal-containing material to the exposed surfaces of mold 10S.

Figure 9:
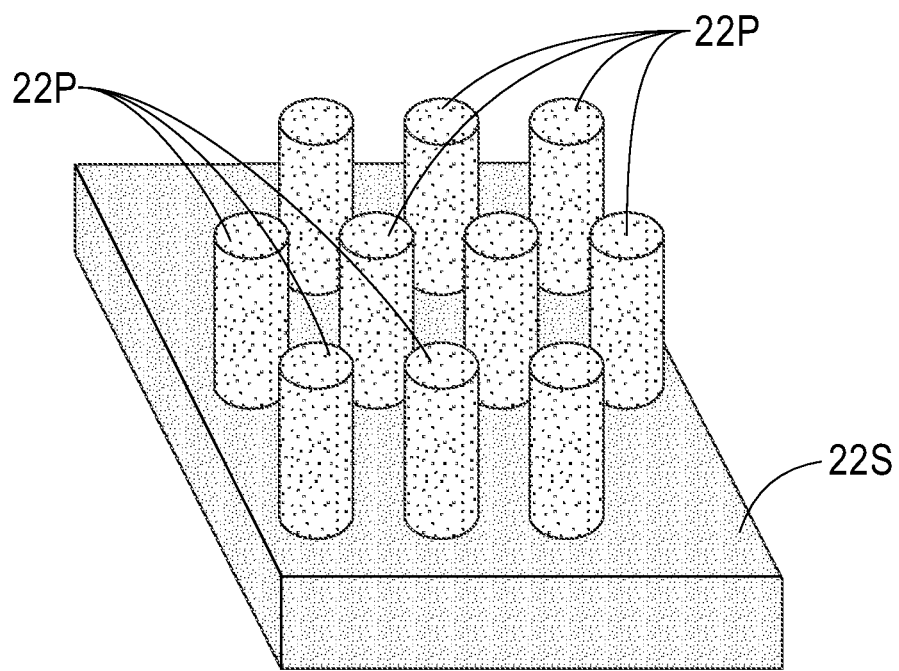
FIG. 9 is a three-dimensional representation of the electrode structure in accordance with an embodiment of the present application.

Referring now to FIG. 9, there is illustrated a three-dimensional representation of the electrode structure (22S, 22P) in accordance with an embodiment of the present application. In this embodiment, each non-random individual articulated feature 22P that provides the non-random topography of the electrode structure is in the shape of a nanorod that extends upward from the electrode base 22S. Additional corresponding wiring and/or associated probe pads required for interpretation of the electrical signal may also be included (not shown).

Figure 10:
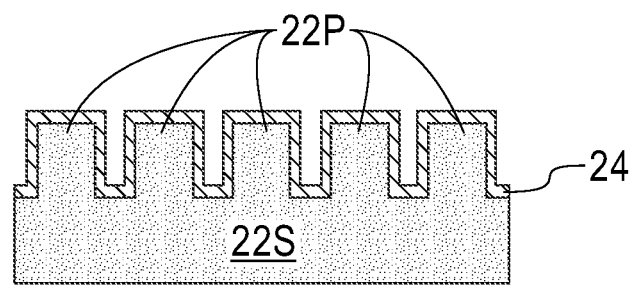
FIG. 10 is a cross sectional view of the exemplary structure of FIG. 8 after the attachment of a biological molecule to the surface of the electrode structure, which is also referred to as a functionalization process.

After forming the electrode structure shown in FIG. 8 or FIG. 9, in order to functionalize the structure to respond as a biosensor, a biological functionalized material 24 can be applied to the surface of the electrode structure (22S, 22P) as shown in FIG. 10, including each non-random individual articulated feature 22P that provides the nanotopography shape of the electrode structure of the present application. Any of the exposed areas of the electrode base 22S may also be coated with the biological functionalization material 24. The electrode structure (22S, 22P) can be used as a component in various biosensors which include other well-known components, such as but not limited to, reference and counter electrode structures.

By "biological functionalization material" it is meant any bioreceptor that binds with a complementary target biomolecule to create a binding event. In the primary embodiment, biochemical reactions involving the biological functionalization material generate an electrical signal which can be conducted by the non-random individual articulated feature 22P of the electrode structure of the present application under an applied electric potential. Examples of biological functionalization materials that can be used in the present application include an oligonucleotide, a nucleic acid, a peptide, a ligand, a protein, an enzyme, or any other material apt to bind with a complementary target biomolecule. When the electrode structure (22P, 22S) of the present application is used for glucose sensing, the biological functionalization material 24 can be composed of glucose oxidase or glucose dehydrogenase.

The biological functionalization material 24 can be applied to the electrode structure (22S, 22P) of the present application utilizing established biological functionalization processes known to those skilled in the art. Such biological functionalization processes typically include a series of chemical reactions that attach the biological functionalization material 24 on the surface of the electrode structure of the present application.

Referring now to FIGS. 11-17, there is illustrated an embodiment of the present application in which a method is disclosed for forming an electrode structure in which an interface is formed between the non-random topography of the electrode structure and the electrode base of the electrode structure.

Figure 11:
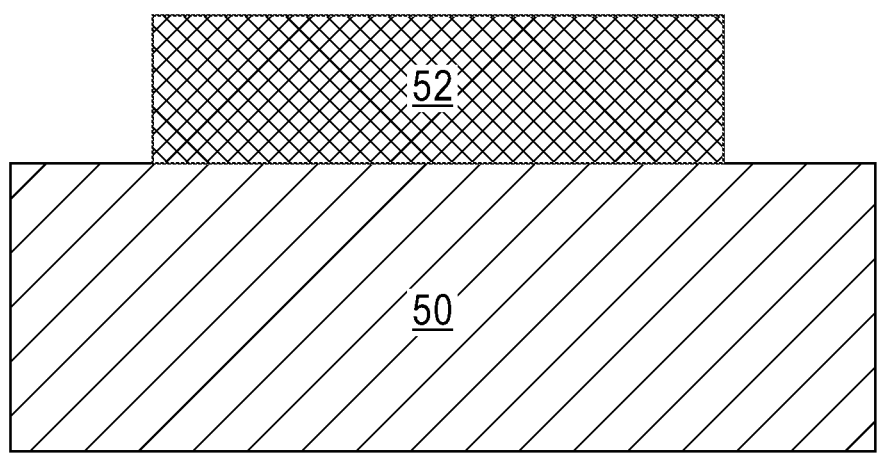
FIG. 11 is a cross sectional view of an exemplary structure including a substrate and an electrode base that can be used in accordance with another embodiment of the present application.

Referring first to FIG. 11, there is illustrated an exemplary structure including a substrate 50 and an electrode base 52 that can be used in accordance with another embodiment of the present application. In some embodiments, other portions of the substrate 50 not containing the electrode base 52 can be protected with a protective dielectric material (not shown).

The substrate 50 that can be used in this embodiment of the present application may include one of materials mentioned above for substrate 10. In one example, substrate 50 may be a semiconductor substrate such as, for example, silicon.

An electrode base 52 can then be formed atop a portion of the substrate 50. The electrode base 52 may be formed by deposition of a conductive material and then patterning the conductive material utilizing any well known patterning process such as, for example, photolithography and reactive ion etching. In one embodiment of the present application, the conductive material may include one of the conductive metal-containing materials mentioned above for conductive metal-containing material 22. In this embodiment, the electrode base 52 has an electrode base shape as defined above.

Figure 12:
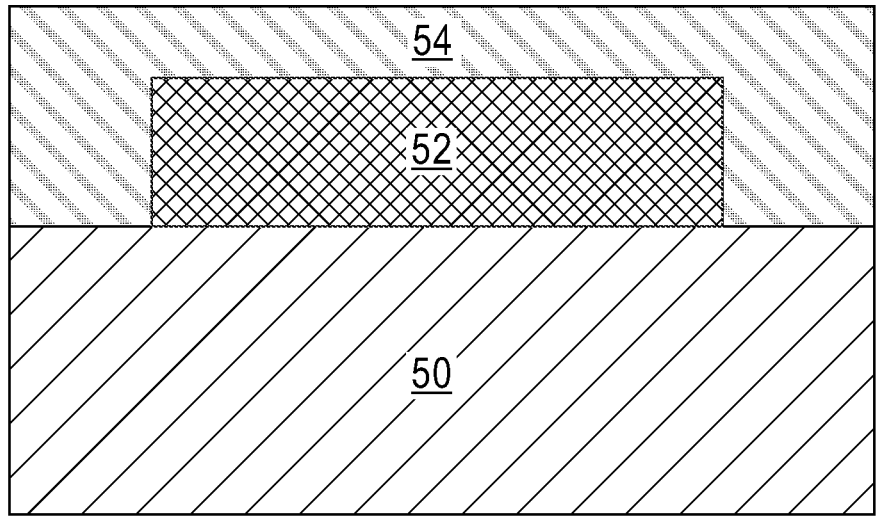
FIG. 12 is a cross sectional view of the exemplary structure of FIG. 11 after depositing a dielectric layer.

Referring now to FIG. 12, there is illustrated the exemplary structure of FIG. 11 after depositing a dielectric layer 54. Dielectric layer 54 may include any hardmask material such as, for example, silicon nitride. The dielectric layer 54 may be formed utilizing any deposition process such as, for example, chemical vapor deposition or plasma enhanced chemical vapor deposition. The dielectric layer 54 may have a height and width that is greater than the height or width of the electrode base 52.

Figure 13:
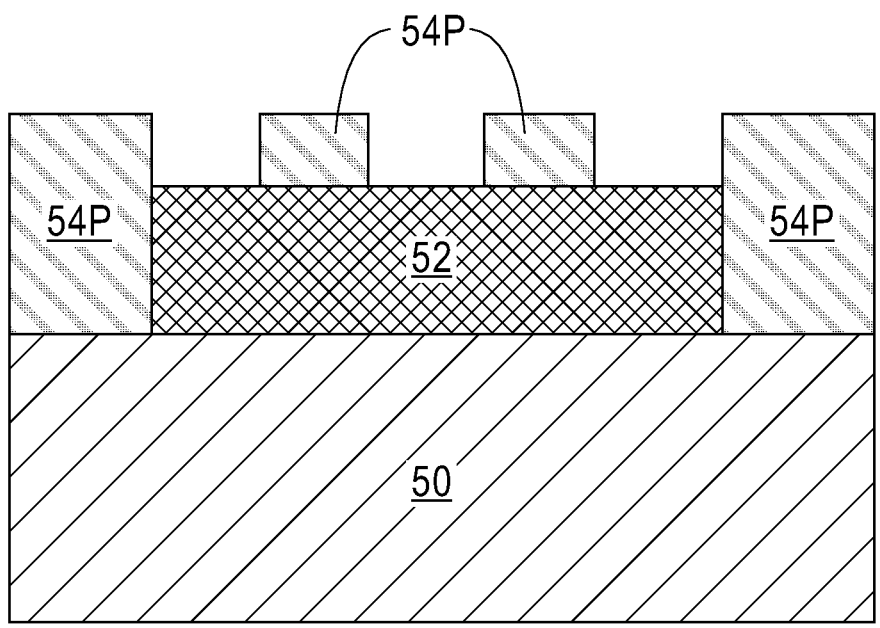
FIG. 13 is a cross sectional view of the exemplary structure of FIG. 12 after forming a nanopattern array in the dielectric layer.

Referring now to FIG. 13, there is illustrated the exemplary structure of FIG. 12 after forming nanotopography on the dielectric layer 54. The nanotopography can be formed utilizing any patterning process including, for example, photolithography and reactive ion etching. The patterning process provides a patterned dielectric layer 54P that has openings that expose portions of the surfaces of the underlying electrode base 52. The openings have the shape and size of a non-random individual articulated feature, as defined above, and thus collectively define the nanotopography shape of the electrode structure of the present application.

Figure 14:
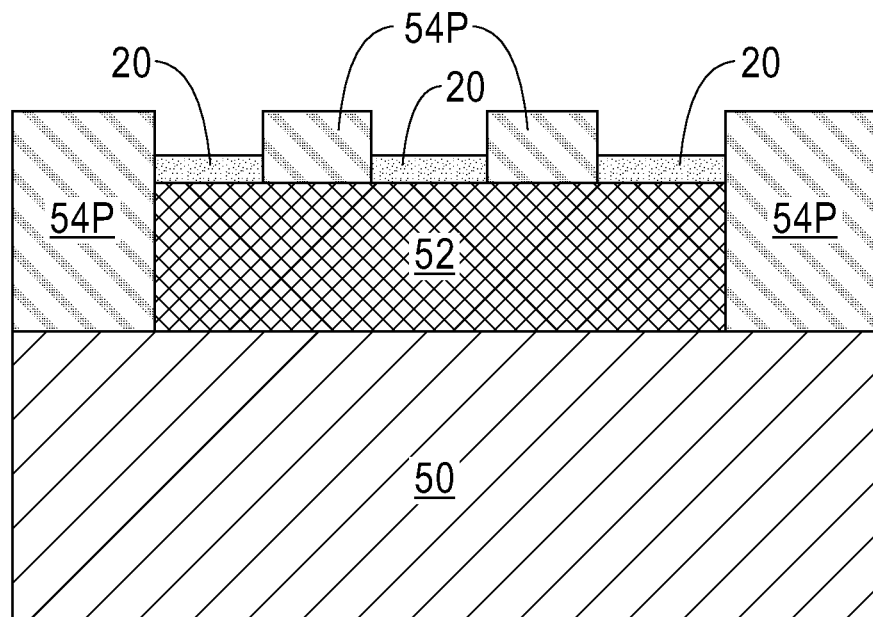
FIG. 14 is a cross sectional view of the exemplary structure of FIG. 13 after forming a metallic seed layer on the exposed surfaces of the electrode base.

Referring now to FIG. 14, there is illustrated the exemplary structure of FIG. 13 after forming a metallic seed layer 20 on exposed surface of the electrode base 52. The metallic seed layer 20 of this embodiment of the present application is the same as the metallic seed layer mentioned in the previous embodiment of the present application. In this embodiment of the present application, the metallic seed layer 20 can be formed by a selective deposition process such that the metallic seed layer 20 is formed only upon the exposed surfaces of the electrode base 52. In an alternate embodiment, metallic seed layer 20 may be rendered unnecessary if electrode base 52 is of a design and material to allow subsequent processing without the presence of a metallic seed layer. Alternatively, a contiguous layer of metallic seed material can be formed as described in the previous embodiment of the present application.

Figure 15:
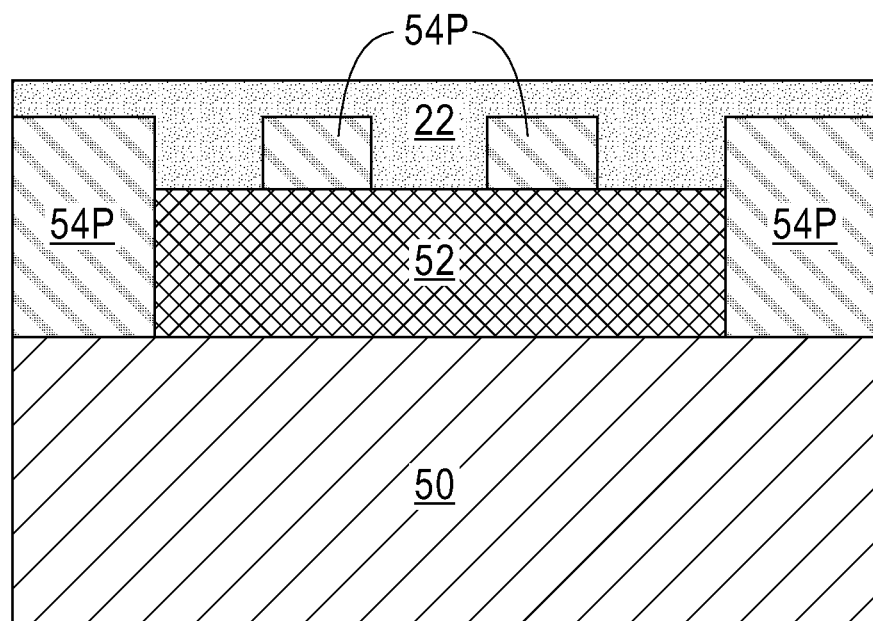
FIG. 15 is a cross sectional view of the exemplary structure of FIG. 14 after electroplating a conductive metal-containing material on the metallic seed layer.

Referring now to FIG. 15, there is illustrated the exemplary structure of FIG. 14 after electroplating a conductive metal-containing material 22 on the metallic seed layer 20. The conductive metal-containing material 22 that is employed in this embodiment of the present application is the same as that described above for the previous embodiment of the present application. The conductive metal-containing material 22 of this embodiment can be formed as described above in the previous embodiment of the present application. Since the metallic seed layer 20 may be composed of the same material as the conductive metal-containing material 22, the metallic seed layer 20 is not separately shown in the drawings of the present application. In this embodiment of the present application, electrode base 52 has the electrode base shape, while the conductive metal-containing material 22 that is formed within the openings present in the patterned dielectric layer 54P collectively define the nanotopography shape of the electrode structure of the present application.

In some embodiments, the conductive metal-containing material 22 may contain a same conductive material as the electrode base 52. In another embodiment, the conductive metal-containing material 22 contains a different conductive material than the conductive material that provides the electrode base 52.

Figure 16:
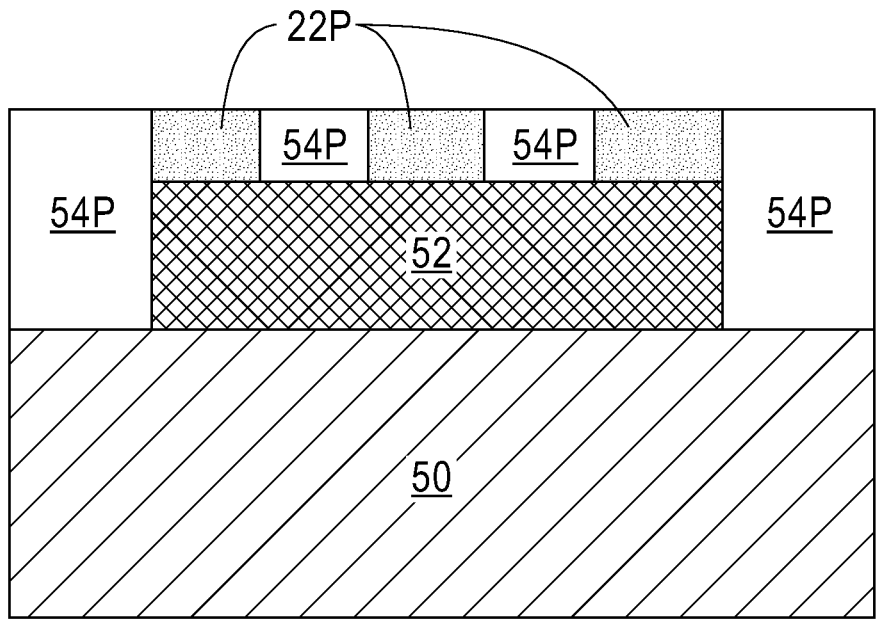
FIG. 16 is a cross sectional view of the exemplary structure of FIG. 15 after removing excess conductive metal-containing material that may be located above the patterned dielectric layer.

Referring now to FIG. 16, there is illustrated the exemplary structure of FIG. 15 after removing excess conductive metal-containing material 22 that may be located above the patterned dielectric layer 54P. After the excess conductive metal-containing material 22 is removed, an electrode structure (52, 22P) is formed that includes the electrode base 52 and non-random individual articulated features 22P that provides the nanotopography shape of the electrode structure of this embodiment of the present application.

In one embodiment of the present application, the removal of the excess conductive metal-containing material 22 may be performed by a planarization process such as, for example, chemical mechanical planarization and/or grinding. In another embodiment of the present application, the removal of the excess conductive metal-containing material 22 may be performed by utilizing at least one etch process such as, for example, a chemical etch back process and/or a reactive ion etch (RIE) process. In either embodiment, the removal process provides a structure in which the topmost surface of each of the non-random individual articulated features 22P is coplanar with the topmost surface of the patterned dielectric layer 54P.

Figure 17:
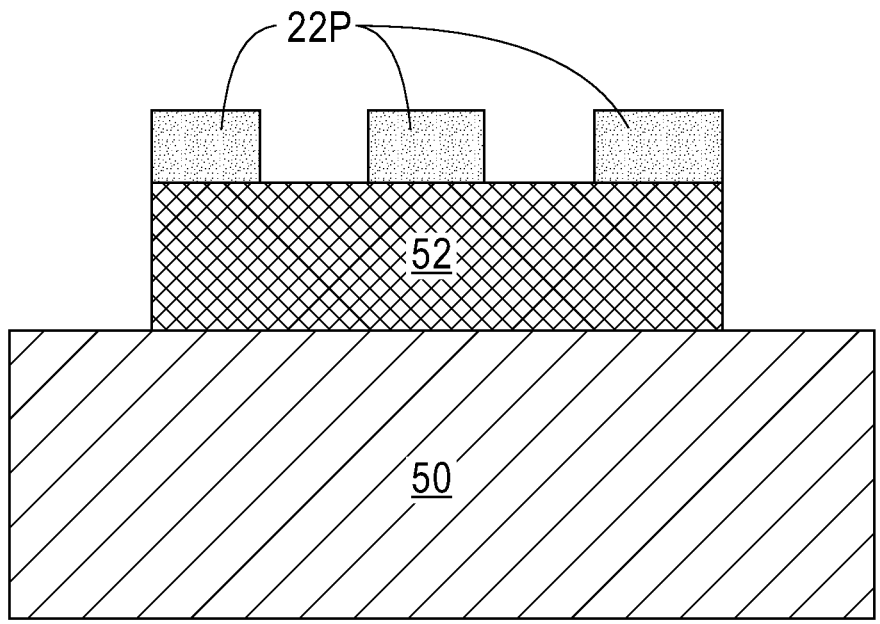
FIG. 17 is a cross sectional view of the exemplary structure of FIG. 16 after removing the patterned dielectric layer.

Referring now to FIG. 17, there is illustrated the exemplary structure of FIG. 16 after removing the patterned dielectric layer 54P. The patterned dielectric layer 54P may be removed utilizing any removal process that is selective in removing the dielectric material that provides the patterned dielectric layer 54P relative to a conductive metal or the material of the substrate 50. In some embodiments, a reactive ion etch may be employed to remove the patterned dielectric layer 54P. In another embodiment, a chemical wet etch process may be used to remove the patterned dielectric layer 54P. In yet another embodiment, patterned dielectric layer 54P may be recessed such that the top surfaces of electrode structure 52 are exposed while the sidewalls of electrode structure 52 remain covered by patterned dielectric layer 54P.

In some embodiments of the present application, the substrate 50 can be removed from beneath the electrode structure (52, 22P) shown in FIG. 17 to provide a freestanding electrode structure (52, 22P). The removal of the substrate 50 may be performed utilizing a planarization process or series of processes such, as for example, chemical mechanical planarization or mechanical grinding. The electrode structure (52, 22P) can be functionalized to respond as a biosensor. Notably, a biological functionalization material as defined above can be applied to the surface of the electrode structure (52, 22P) provided in FIGS. 11-17.

Referring now to FIGS. 18-22, there is illustrated an embodiment of the present application in which a method is disclosed for forming an electrode structure in which an interface is formed between the non-random topography of the electrode structure and the electrode base of the electrode structure. This embodiment of the present application begins by first providing the exemplary structure shown in FIG. 11.

Figure 18:
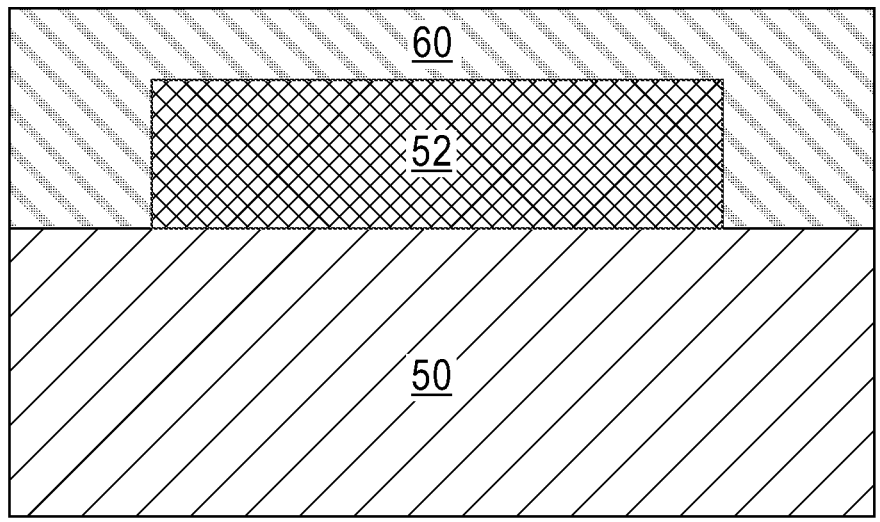
FIG. 18 is a cross sectional view of the exemplary structure of FIG. 11 after depositing a photoresist layer.

Referring first to FIG. 18, there is illustrated the exemplary structure of FIG. 11 after depositing a photoresist layer 60. Photoresist layer 60 may include a positive-tone or negative-tone photoresist material. The photoresist layer 60 may be formed utilizing any deposition process such as, for example, spin-on coating. The photoresist layer 60 may have a height and width that is greater than the height or width of the electrode base 52.

Figure 19:
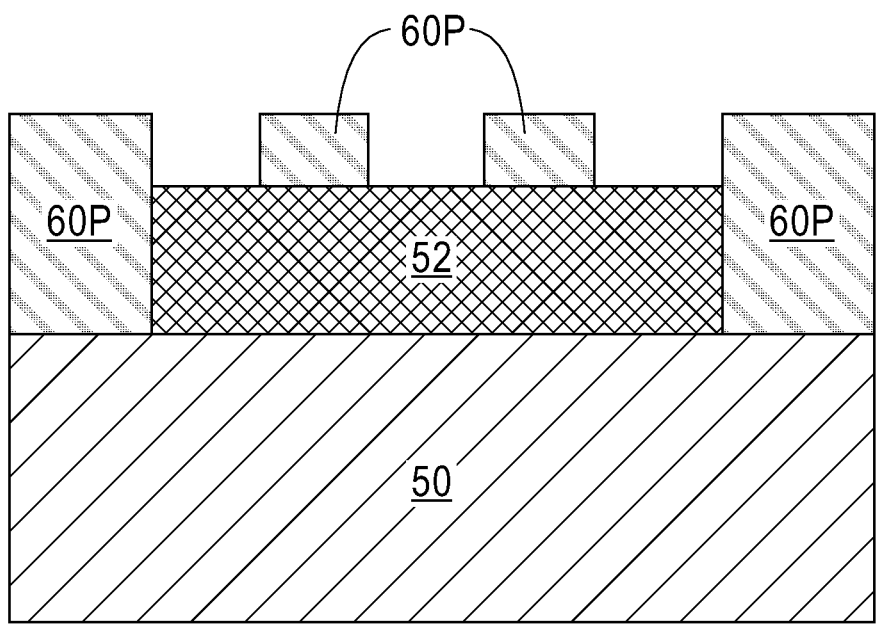
FIG. 19 is a cross sectional view of the exemplary structure of FIG. 18 after forming a nanopattern array in the photoresist layer.

Referring now to FIG. 19, there is illustrated the exemplary structure of FIG. 18 after patterning the photoresist layer 60. The patterning can be performed by exposing and developing the photoresist layer utilizing photolithography. The nanopatterning provides a patterned photoresist layer 60P including openings that expose surfaces of the underlying electrode base 52. The openings have the shape and size of a non-random individual articulated feature, as defined above, and thus collectively define the nanotopography shape of the electrode structure of the present application.

Figure 20:
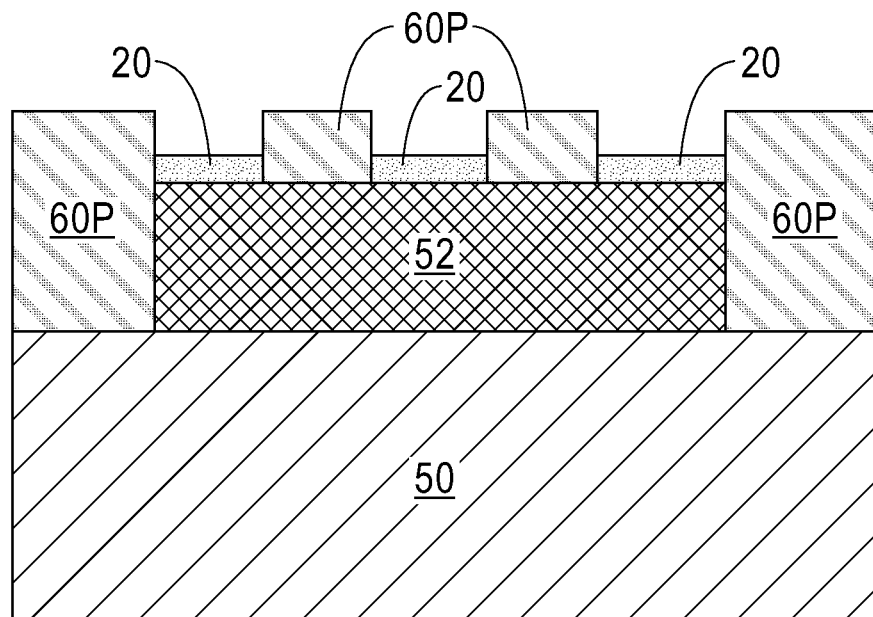
FIG. 20 is a cross sectional view of the exemplary structure of FIG. 19 after forming a metallic seed layer on exposed surfaces of the electrode base.

Referring now to FIG. 20, there is illustrated the exemplary structure of FIG. 19 after forming a metallic seed layer 20 on exposed surface of the electrode base 52. The metallic seed layer 20 of this embodiment of the present application is the same as the metallic seed layer mentioned in the previous embodiment of the present application. In this embodiment of the present application, the metallic seed layer 20 can be formed by a selective deposition process such that the metallic seed layer 20 is formed only upon the exposed surfaces of the electrode base 52. Alternatively, a contiguous layer of metallic seed material can be formed as described in the previous embodiment of the present application.

Figure 21:
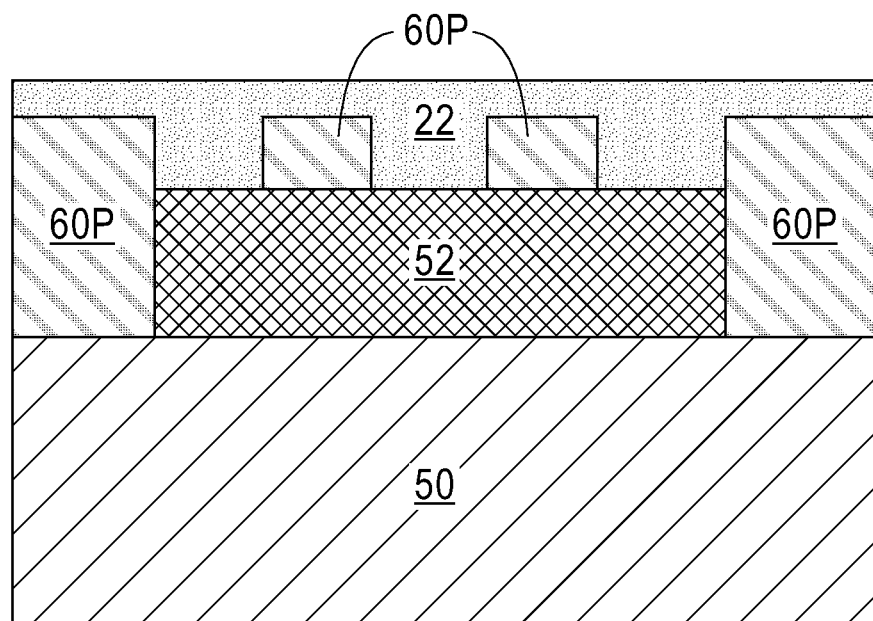
FIG. 21 is a cross sectional view of the exemplary structure of FIG. 20 after electroplating a conductive metal-containing material.

Referring now to FIG. 21, there is illustrated the exemplary structure of FIG. 20 after electroplating a conductive metal-containing material 22 on the metallic seed layer 20. The conductive metal-containing material 22 that is employed in this embodiment of the present application is the same as that described above for the previous embodiment of the present application. The conductive metal-containing material 22 of this embodiment can be formed as described above in the previous embodiment of the present application. Since the metallic seed layer 20 may be composed of the same material as the conductive metal-containing material 22, the metallic seed layer 20 is not separately shown in the drawings of the present application. In this embodiment of the present application, electrode base 52 has the electrode base shape, while the conductive metal-containing material 22 that is formed within the openings present in the patterned photoresist layer 60P collectively define the nanotopography shape of the electrode structure of the present application.

In some embodiments, the conductive metal-containing material 22 may contain a same conductive material as the electrode base 52. In another embodiment, the conductive metal-containing material 22 contains a different conductive material than the conductive material that provides the electrode base 52.

Figure 22:
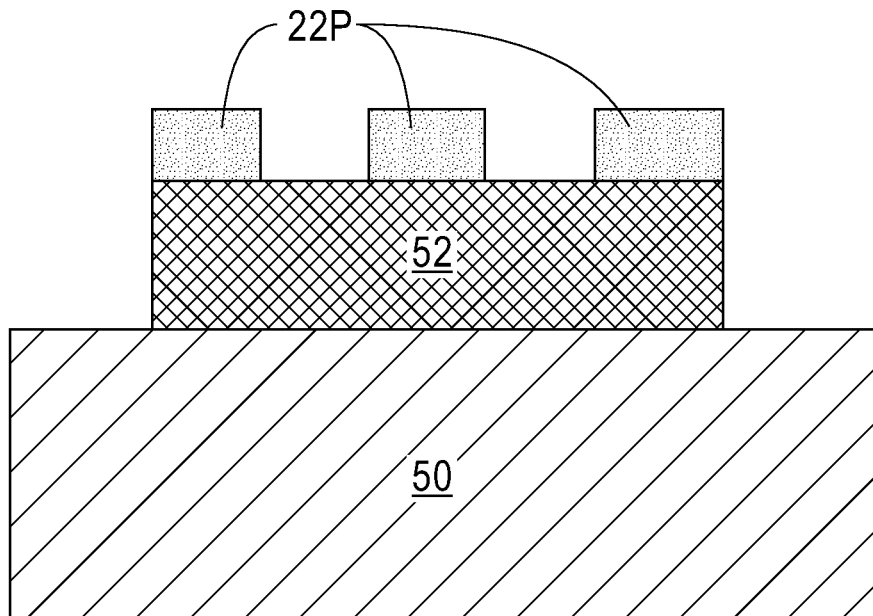
FIG. 22 is a cross sectional view of the exemplary structure of FIG. 21 after performing a photoresist lift-off process.

Referring now to FIG. 22, there is illustrated the exemplary structure of FIG. 21 after performing a lift-off process to remove the excess patterned photoresist layer 60P. After performing the lift-off process, an electrode structure (52, 22P) is formed that includes the electrode base 52 and non-random individual articulated features 22P that provides the nanotopography shape of the electrode structure of this embodiment of the present application.

The lift-off process that can be used in the present application includes any conventional lift process that can remove the material that provides the patterned photoresist layer 60P. During the lift-off process portions of the conductive metal-containing material 22 located directly atop the patterned photoresist layer 54P can be removed. After performing the lift-off process, a planarization process may be used to provide the non-random individual articulated features 22P of the electrode structure of this embodiment of the present application.

In some embodiments of the present application, the substrate 50 can be removed from beneath the electrode structure (52, 22P) shown in FIG. 22 to provide a free-standing electrode structure (52, 22P). The removal of the substrate 50 may be performed utilizing a planarization process or series of processes such as, for example, chemical mechanical planarization and mechanical grinding. The electrode structure (52, 22P) can be functionalized with a biologically active layer to respond as a biosensor. Notably, a biological functionalization material as defined above can be applied to the surface of the electrode structure (52, 22P) provided in FIGS. 18-22.

Figure 23:
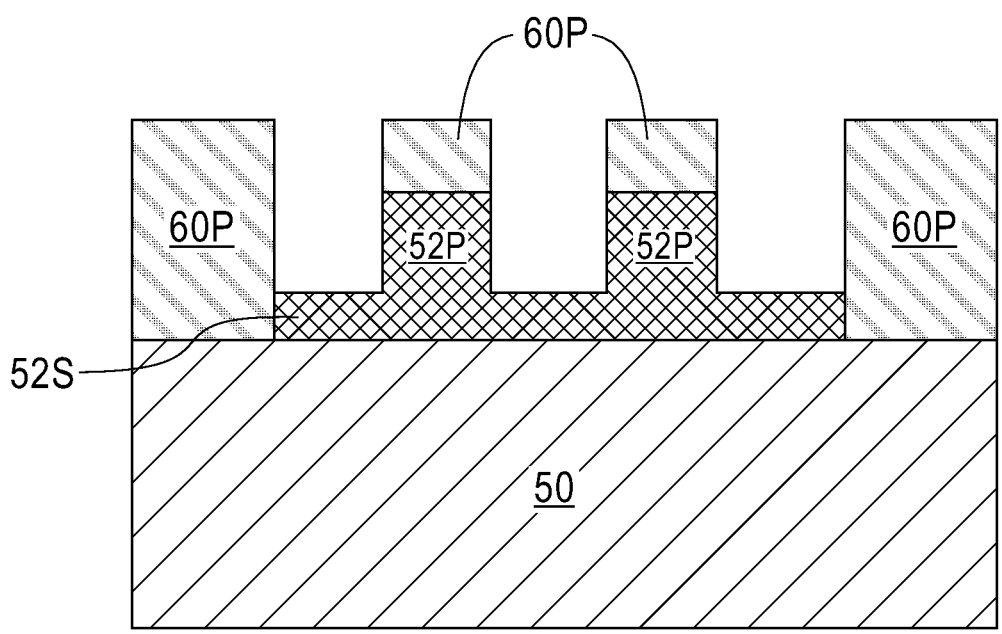
FIG. 23 is a cross sectional view of the exemplary structure of FIG. 19 after etching the exposed portions of the electrode base utilizing the patterned photoresist layer as an etch mask.
Figure 24:
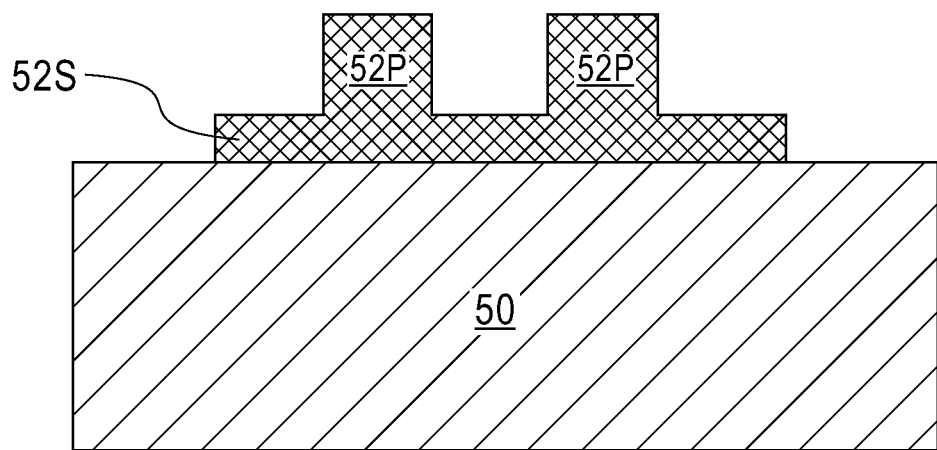
FIG. 24 is a cross sectional view of the exemplary structure of FIG. 23 after removing the patterned photoresist layer.

Referring now to FIGS. 23-24, there is illustrated an embodiment of the present application in which a method is disclosed for forming an electrode structure in which no interface is formed between the non-random topography of the electrode structure and the electrode base of the electrode structure. This embodiment of the present application begins by providing either the exemplary structure shown in FIG. 13 or FIG. 19. For illustrative purposes, the exemplary structure shown in FIG. 19 is shown. When the exemplary structure shown in FIG. 13 is used, the etching of the exposed portions of the electrode base 52 as disclosed herein below can be used utilizing the patterned dielectric layer 54P as an etch mask. After etching the patterned dielectric layer 54P can be removed as disclosed in the second embodiment mentioned above. In this embodiment of the present application and unlike the previous embodiments, the initial electrode base 52 does not yet have the electrode base shape; in this embodiment the electrode base that does not have the electrode base shape may be referred to merely as an electrode base material. Instead, the electrode base shape is defined by the openings that are present in the patterned photoresist layer 60 and the depth of the etch, while the portions of the patterned photoresist layer 60P atop the electrode base material and the depth of the etch collectively define the nanotopography shape of the electrode structure of the present application.

Referring now to FIG. 23, there is illustrated the exemplary structure of FIG. 19 after etching the exposed portions of the electrode base material utilizing the patterned photoresist layer 60P as an etch mask. The etching of the exposed portions of the electrode base material provides an electrode structure of the present application. The electrode structure includes electrode base 52S having non-random topography provided by individual articulated features 52P located on one surface of the electrode base 52S. In accordance with this embodiment of the present application, the electrode base 52S and the non-random topography provided by the individual articulated features 52P are of uniform construction and uniform composition.

The etching of the exposed portions of the electrode base material can be performed utilizing an anisotropic etch process. In one example, the anisotropic etch process is a dry etching process such as, for example, reactive ion etching. In another example, the anisotropic etch process is a chemical wet etch process in which a chemical etchant that selectively removes the material that provides the electrode base material relative to photoresist material.

Referring now to FIG. 24, there is illustrated the exemplary structure of FIG. 23 after removing the patterned photoresist layer 60P. The removal of the patterned photoresist may be performed utilizing any photoresist stripping process such, as for example, oxygen plasma-based ashing. As is shown, in FIG. 24, the removal of the patterned photoresist layer 60P from the exemplary structure shown in FIG. 23 provides an electrode structure that includes electrode base 52S having non-random topography provided by individual articulated features 52P located on one surface of the electrode base 52S; the electrode base 52S which now has electrode base shape is composed of remaining portions of electrode base material. In accordance with this embodiment of the present application, the electrode base 52S and the non-random topography provided by the individual articulated features 52P are of uniform construction and uniform composition.

In some embodiments of the present application, the substrate 50 can be removed from beneath the electrode structure (52S, 52P) shown in FIG. 24 to provide a free-standing electrode structure (52S, 52P). The removal of the substrate 50 may be performed utilizing a planarization process or series of processes such as, for example, chemical mechanical planarization and mechanical grinding. The electrode structure (52S, 52P can be functionalized to respond as a biosensor. Notably, a biological functionalized material as defined above can be applied to the surface of the electrode structure (52S, 52P) provided in FIGS. 23-24.

While the present application has been particularly shown and described with respect to preferred embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A method of forming an electrode structure, the method comprising:
    providing an electrode base having an electrode base shape on a substrate;
    forming a patterned material layer on and surrounding the electrode base, wherein the patterned material layer contains openings that physically expose the electrode base and define a nanotopography shape of the electrode structure;
    forming a metallic seed layer on the physically exposed surfaces of the electrode base and within the openings;
    electroplating a conductive metal-containing material on the metallic seed layer and within the openings to provide the electrode structure comprising the electrode base having the electrode base shape and the conductive metal-containing material having the nanotopography shape;
    removing the patterned material layer; and
    attaching a biological functionalization material to the electrode structure.

2. The method of claim 1, wherein the patterned material layer is composed of a dielectric material, and the substrate is composed of a semiconductor material.

3. The method of claim 1, wherein the patterned material layer is composed of a photoresist material, and the substrate is composed of a semiconductor material.

4. The method of claim 1, further comprising: removing the substrate, wherein the removing of the substrate is performed between the removing of the patterned material layer and the attaching of the biological functionalization material to the electrode structure.

5. The method of claim 1, wherein the metallic seed layer and the conductive metal-containing material comprise a same metal or metal alloy.

6. The method of claim 1, wherein the biological functionalization material is composed of an oligonucleotide, a nucleic acid, a peptide, a ligand, a protein, an enzyme, or any other material apt to bind with a complementary target biomolecule.

7. The method of claim 6, wherein the biological functionalization material is composed of glucose oxidase or glucose dehydrogenase.

8. The method of claim 1, wherein an interface is present between the electrode base shape and the nanotopography shape.

9. The method of claim 1, wherein the providing of the electrode base having the electrode base shape comprises:
    depositing a conductive material on the substrate; and
    patterning the conductive material.

10. The method of claim 9, wherein the conductive material is a conductive metal-containing material selected from an elemental metal and an alloy containing one of more elemental metals.

11. The method of claim 10, wherein the elemental metal is platinum, copper, silver, gold, tungsten, aluminum, iron, palladium, nickel, titanium or zirconium.

12. The method of claim 1, wherein the forming of the metallic seed layer comprises a selective deposition process.

13. The method of claim 1, wherein the conductive metal-containing material has a topmost surface that is coplanar with a topmost surface of the patterned material layer.

14. The method of claim 13, wherein the electroplating of the conductive metal-containing material further comprises removing excess conductive metal-containing material that extends outside of the openings.

15. The method of claim 14, wherein the removing of the excess conductive metal-containing material comprises a planarization process or an etch back process.

16. The method of claim 1, wherein the removing of the patterned material layer comprises recessing the patterned material layer to physically expose a topmost surface of the electrode structure, while maintaining said patterned material layer along the sidewalls of the electrode structure.

17. The method of claim 1, wherein the removing of the patterned material layer comprises a reactive ion etch or a chemical wet etch.

18. A method of forming an electrode structure, the method comprising:
    providing an electrode base having an electrode base shape on a substrate;
    forming a patterned material layer on and surrounding the electrode base, wherein the patterned material layer contains openings that physically expose the electrode base and define a nanotopography shape of the electrode structure;
    electroplating a conductive metal-containing material within the openings to provide the electrode structure comprising the electrode base having the electrode base shape and the conductive metal-containing material having the nanotopography shape;
    removing the patterned material layer; and
    attaching a biological functionalization material to the electrode structure.

19. The method of claim 18, further comprising: removing the substrate, wherein the removing of the substrate is performed between the removing of the patterned material layer and the attaching of the biological functionalization material to the electrode structure.

20. The method of claim 18, wherein an interface is present between the electrode base shape and the nanotopography shape.

* * * * *